(12) United States Patent
Shibasaki et al.

(10) Patent No.: US 9,493,492 B2
(45) Date of Patent: Nov. 15, 2016

(54) COMPOUND, MANUFACTURING METHOD THEREFOR, AND METHOD FOR MANUFACTURING OPTICALLY ACTIVE α-AMINOPHOSPHONATE DERIVATIVE

(71) Applicant: Microbial Chemistry Research Foundation, Tokyo (JP)

(72) Inventors: Masakatsu Shibasaki, Tokyo (JP); Naoya Kumagai, Tokyo (JP); Liang Yin, Tokyo (JP); Youmei Bao, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 0 days.

(21) Appl. No.: 14/900,696

(22) PCT Filed: Oct. 8, 2013

(86) PCT No.: PCT/JP2013/077343
§ 371 (c)(1),
(2) Date: Dec. 22, 2015

(87) PCT Pub. No.: WO2014/207951
PCT Pub. Date: Dec. 31, 2014

(65) Prior Publication Data
US 2016/0145278 A1 May 26, 2016

(30) Foreign Application Priority Data

Jun. 27, 2013 (JP) ................. 2013-134633

(51) Int. Cl.
C07F 9/40 (2006.01)
B01J 31/24 (2006.01)
C07F 9/50 (2006.01)
(Continued)

(52) U.S. Cl.
CPC .............. *C07F 9/4062* (2013.01); *B01J 31/24* (2013.01); *C07F 9/36* (2013.01); *C07F 9/4009* (2013.01); *C07F 9/4015* (2013.01); *C07F 9/4056* (2013.01); *C07F 9/5054* (2013.01); *C07F 9/65683* (2013.01); *B01J 2231/34* (2013.01); *B01J 2531/16* (2013.01)

(58) Field of Classification Search
CPC ..... C07F 9/4062; C07F 9/5054; B01J 31/24; B01J 2231/34; B01J 2531/16
USPC .......................... 558/166, 87, 144
See application file for complete search history.

(56) References Cited

FOREIGN PATENT DOCUMENTS

JP 2009-151191 10/1997
JP 2007-302568 11/2007
JP 2011-046661 10/2011

OTHER PUBLICATIONS

Atherton, et al., "Synthesis and Structure-Activity Relationships of Antibacterial Phosphonopeptides Incorporating (1-Aminoethyl)phosphonic Acid and (Aminomethyl)phosphonic Acid," J. Med. Chem., vol. 29, pp. 29-40 (1986).

(Continued)

*Primary Examiner* — Kristin Vajda
(74) *Attorney, Agent, or Firm* — Carmody Torrance Sandak & Hennessey LLP

(57) ABSTRACT

A method for producing a compound represented by General Formula (1), the method including:
reacting a compound represented by General Formula (3) and a compound represented by General Formula (4):

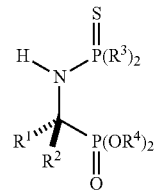

General Formula (1)

where $R^1$ and $R^2$ each represent aliphatic group which may have substituent, or aromatic group which may have substituent (with the proviso that $R^1$ and $R^2$ are different groups), $R^3$ represents aromatic group which may have substituent, and $R^4$ represents aliphatic group which may have substituent, or aromatic group which may have substituent,

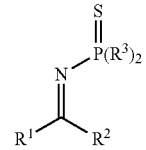

General Formula (3)

where $R^1$ and $R^2$ each represent aliphatic group which may have substituent, or aromatic group which may have substituent (with the proviso that $R^1$ and $R^2$ are different groups), and $R^3$ represents aromatic group which may have substituent,

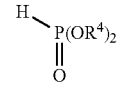

General Formula (4)

where $R^4$ represents aliphatic group which may have substituent, or aromatic group which may have substituent.

6 Claims, No Drawings

(51) Int. Cl.
    *C07F 9/6568*    (2006.01)
    *C07F 9/36*      (2006.01)

(56) References Cited

OTHER PUBLICATIONS

Allen, et al., "Phosphonopeptides, A New Class of Synthetic Antibacterial Agents," Nature, vol. 272, p. 56-58 (Mar. 2, 1978).

Smith, et al., "Macrocyclic Inhibitors of Penicillopepsin. 3. Design, Synthesis, and Evaluation of an Inhibitor Bridged Between P2 and P1," J. Am. Chem. Soc., vol. 120, pp. 4622-4628 (1998).

Hiratake, et al., "Aminophosphonic and Aminoboronic Acids as Key Elements of a Transition State Analogue Inhibitor of Enzymes," Bioscience, Biotechnology, and Biochemistry, vol. 61, No. 2, pp. 211-218 (1997).

Hirschmann, et al., "Peptide Synthesis Catalyzed by an Antibody Containing a Binding Site for Variable Amino Acids," Science, vol. 265, pp. 234-237 (Jul. 8, 1994).

Kuliszewska, et al., "Preparation of α-Aminobenzylphosphonic Acids with a Stereogenic Quaternary Carbon Atom via Microscopically Configurationally Stable α-Aminobenzyllithiums," Chem. Eur. J., vol. 14, pp. 8603-8614 (2008).

Davis, et al., "Asymmetric Synthesis of α-Methylphosphophenylalanine Derivatives Using Sulfinimine-Derived Enantiopure Aziridine-2-Phosponates," Organic Letters, vol. 1, No. 7, pp. 1053-1055 (1999).

Davis, et al., "Asymmetric Synthesis of Quaternary α-Amino Phosphonates Using Sulfinimines," Organic Letters, vol. 3, No. 11, pp. 1757-1760 (2001).

Chen, et al., "A New and Convenient Asymmetric Synthesis of α-Amino- and α-Alkyl-α-aminophosphonic Acids Using N-tert-Butylsulfinyl Imines as Chiral Auxiliaries," Synthesis, No. 24, pp. 3779-3786 (2007).

Nakamura, et al., "Catalytic Enantioselective Hydrophosphonylation of Ketimines Using Cinchona Alkaloids," Journal of the American Chemical Society, vol. 131, pp. 18240-18241 (Dec. 3, 2009).

Belov, et al., "Optically Active α-Aminoethylphosphonic Acids and Their Ethylesters," Izvestiya Akademii Nauk SSSR, Seriya Khimicheskaya, vol. 7, pp. 1596-1599 (1977) (Compound "(II)", Tables 1-3).

Belov, et al., "Sorbents with Optically Active α-Aminoethylphosphonic Acid Groups for Ligand Exchange Chromatography of Racemates," Izvestiya Akademii Nauk SSSR, Seriya Khimicheskaya, vol. 8, pp. 1856-1860 (1977) (p. 1856, middle part, compounds).

Chekhlov, et al., "Absolute Configuration of (+)-(1-amino-1-methylpropyl) Phosphonic Acid," Izvestiya Akademii Nauk SSSR, Seriya Khimicheskaya, vol. 12, pp. 2821-2823 (1986) (p. 2822, compound 4).

Davis, et al., "Asymmetric Synthesis of Polyfunctionalized Pyrrolidines from Sulfinimine-Derived Pyrrolidine 2-Phosphonates. Synthesis of Pyrrolidine 225C," Organic Letters, vol. 8, No. 11, pp. 2273-2276 (2006).

Bera, et al., "Enantioselective Synthesis of α-Amino-γ-sulfonyl Phosphonates with a Tetrasubstituted Chiral α-Carbon via Quinine-Squaramide-Catalyzed Michael Addition of Nitrophosphonates to Vinyl Sulfones," Adv. Synth. Catal., vol. 355, pp. 1265-1270 (2013).

Wilt, et al., "A Diastereo- and Enantioselective Synthesis of α-Substituted anti-α,β-Diaminophosphonic Acid Derivatives," Chem. Commun., vol. 35, pp. 4177-4179 (Sep. 2008).

Dembkowski, et al., "β-Phosphorylated Five Membered Ring Nitroxides. Synthesis and EPR Study," Free Radical Research Communications, vol. 19, Supplement, pp. S23-S32 (1993).

Stipa, et al., "β-Phosphorylated Five-Membered Ring Nitroxides: Synthesis and ESR Study of 2-Phosphonyl-4-(hydroxymethyl)pyrrolidine Aminoxyl Radicals," J. Org. Chem., vol. 58, pp. 4485-4468 (1993).

Ordonez, et al., "An Overview of Stereoselective Synthesis of α-Aminophosphonic Acids and Derivatives," Tetrahedron, vol. 65, pp. 17-49 (2009).

Yin, et al., "Catalytic Asymmetric Hydrophosphonylation of Ketimines," Journal of the American Chemical Society, vol. 135, pp. 10338-10341 (2013).

COMPOUND, MANUFACTURING METHOD THEREFOR, AND METHOD FOR MANUFACTURING OPTICALLY ACTIVE α-AMINOPHOSPHONATE DERIVATIVE

TECHNICAL FIELD

The present invention relates to a method for efficiently synthesizing an optically active α-aminophosphonic acid derivative which is useful as a starting material of a candidate substance of a drug. Specifically, the present invention relates to a novel compound, a method for efficiently synthesizing the novel compound, a method for synthesizing the optically active α-aminophosphonic acid derivative using the novel compound, and a novel optically active α-aminophosphonic acid derivative.

BACKGROUND ART

Optically active α-aminophosphonic acid derivatives are useful for the synthesis of candidate compounds of pharmaceutical drugs such as antibacterial agents, anti-HIV drugs, and enzyme inhibitors (see, for example, NPLs 1 to 5).

Generally employed methods for producing optically active α-aminophosphonic acid derivatives are, for example, methods using chiral auxiliary groups for increasing stereoselectivity (see, for example, NPLs 6 to 9).

These techniques, however, use expensive chiral auxiliary groups in a large amount (an equimolar amount or more) and the chiral auxiliary groups cannot be recovered after use, having a problem that they are not economical.

Other proposed production methods include a method using, as a catalyst, Cinchona Alkaloid such as quinine, adding diphenyl phosphate to a specific ketimine to obtain an adduct, and synthesizing an optically active α-aminophosphonic acid derivative from the adduct (see, for example, NPL 10).

This technique, however, has a problem that stereoselectivity is low unless at least one of two substituents binding to carbon of the C=N bond of the ketimine is an aromatic hydrocarbon group, which imposes limitation on synthesized optically active α-aminophosphonic acid derivatives.

At present, therefore, there is a need for a novel production method capable of synthesizing various optically active α-aminophosphonic acid derivatives without using chiral compounds in a large amount.

CITATION LIST

Non-Patent Literatures

NPL 1 Frank R. Atherton, et al., J. Med. Chem., 1986, 29, 29.
NPL 2 J. G. ALLEN, et al., Nature, 1978, 272, 56
NPL 3 Whitney W Smith, et al., J. Am. Chem. Soc., 1998, 120, 4622
NPL 4 Jun Hiratake, et al., Biosci., Biotechnol., Biochem. 1997, 61, 211
NPL 5 Ralph Hirschmann, et al., Science, 1994, 265, 234
NPL 6 Edyta Kuliszewska, et al., Chem. Eur. J., 2008, 14, 8603
NPL 7 Franklin A. Davis, et al., Org. Lett., 1999, 1, 1053
NPL 8 Franklin A. Davis, et al., Org. Lett., 2001, 3, 1757
NPL 9 Qianyi Chen, et al., Synthesis, 2007, 24, 3779
NPL 10 Shuichi Nakamura, et al., J. AM. CHEM. SOC., 2009, 131, 18240

SUMMARY OF INVENTION

Technical Problem

The present invention aims to solve the above existing problems and achieve the following object. That is, an object of the present invention is to provide a novel production method capable of synthesizing various optically active α-aminophosphonic acid derivatives without using chiral compounds in a large amount, a novel compound obtained by the production method, a method for producing optically active α-aminophosphonic acid derivatives using the novel compound, and a novel optically active α-aminophosphonic acid derivative.

Solution to Problem

Means for solving the above problems are as follows.

<1> A method for producing an optically active α-aminophosphonic acid derivative, the method including:

converting a compound represented by the following General Formula (1) to an optically active α-aminophosphonic acid derivative represented by the following General Formula (2):

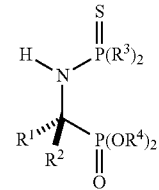

General Formula (1)

where in the General Formula (1), $R^1$ and $R^2$ each represent an aliphatic group which may have a substituent, or an aromatic group which may have a substituent (with the proviso that $R^1$ and $R^2$ are different groups), $R^3$ represents an aromatic group which may have a substituent, and $R^4$ represents an aliphatic group which may have a substituent, or an aromatic group which may have a substituent,

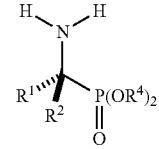

General Formula (2)

where in the General Formula (2), $R^1$ and $R^2$ each represent an aliphatic group which may have a substituent, or an aromatic group which may have a substituent (with the proviso that $R^1$ and $R^2$ are different groups), and $R^4$ represents an aliphatic group which may have a substituent, or an aromatic group which may have a substituent.

<2> An optically active α-aminophosphonic acid derivative represented by the following General Formula (2):

General Formula (2)

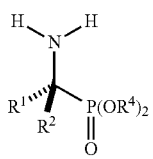

where in the General Formula (2), $R^1$ and $R^2$ each represent an aliphatic group which may have a substituent, or an aromatic group which may have a substituent (with the proviso that $R^1$ and $R^2$ are different groups), and $R^4$ represents an aliphatic group which may have a substituent, or an aromatic group which may have a substituent (with the proviso that when the $R^1$ is the aromatic group which may have a substituent, the $R^4$ is the aliphatic group which may have a substituent).

<3> A compound represented by the following General Formula (1):

General Formula (1)

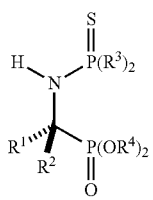

where in the General Formula (1), $R^1$ and $R^2$ each represent an aliphatic group which may have a substituent, or an aromatic group which may have a substituent (with the proviso that $R^1$ and $R^2$ are different groups), $R^3$ represents an aromatic group which may have a substituent, and $R^4$ represents an aliphatic group which may have a substituent, or an aromatic group which may have a substituent.

<4> A method for producing the compound represented by General Formula (1) according to <3>, the method including:

reacting a compound represented by the following General Formula (3) and a compound represented by the following General Formula (4):

General Formula (3)

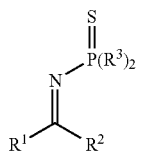

where in the General Formula (3), $R^1$ and $R^2$ each represent an aliphatic group which may have a substituent, or an aromatic group which may have a substituent (with the proviso that $R^1$ and $R^2$ are different groups), and $R^3$ represents an aromatic group which may have a substituent, General Formula (4)

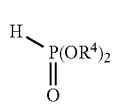

where in the General Formula (4), $R^4$ represents an aliphatic group which may have a substituent, or an aromatic group which may have a substituent.

Advantageous Effects of Invention

The present invention can solve the above existing problems and achieve the above object, and can provide a novel production method capable of synthesizing various optically active α-aminophosphonic acid derivatives without using chiral compounds in a large amount, a novel compound obtained by the production method, a method for producing optically active α-aminophosphonic acid derivatives using the novel compound, and a novel optically active α-aminophosphonic acid derivative.

DESCRIPTION OF EMBODIMENTS

Steric configurations in the chemical formulas and the general formulas described in the present specification and claims are absolute configurations unless otherwise specified.

(Compound Represented by General Formula (1))

A compound of the present invention is represented by the following General Formula (1):

General Formula (1)

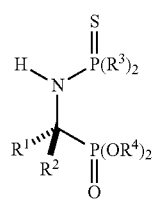

where in the General Formula (1), $R^1$ and $R^2$ each represent an aliphatic group which may have a substituent, or an aromatic group which may have a substituent (with the proviso that $R^1$ and $R^2$ are different groups), $R^3$ represents an aromatic group which may have a substituent, and $R^4$ represents an aliphatic group which may have a substituent, or an aromatic group which may have a substituent.

<Aliphatic Group which May have a Substituent>

The aliphatic group in the aliphatic group which may have a substituent represented by the $R^1$, the $R^2$, and the $R^4$ may be linear, branched, or cyclic (an alicyclic group).

The aliphatic group in the aliphatic group which may have a substituent represented by the $R^1$, the $R^2$, and the $R^4$ may be a saturated aliphatic group or an unsaturated aliphatic group.

The aliphatic group is preferably an aliphatic hydrocarbon group.

The number of carbon atoms of the aliphatic group which may have a substituent is not particularly limited and may be appropriately selected depending on the intended purpose, but is preferably 1 to 20, more preferably 1 to 10. Note that, when the aliphatic group which may have a substituent has a substituent, the number of carbon atoms of the aliphatic group which may have a substituent refers to the total number of carbon atoms including the number of carbon atoms of the substituent.

Examples of hydrocarbon groups in the saturated aliphatic group include alkyl groups.

The number of carbon atoms of the linear or branched alkyl group in the saturated aliphatic group is preferably 1 to 20, more preferably 1 to 15, particularly preferably 1 to 10.

The cyclic alkyl group in the saturated aliphatic group may have a monocyclic structure or a polycyclic structure, and the number of carbon atoms of the cyclic alkyl group is preferably 3 to 10.

Examples of the linear or branched alkyl include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-methylbutyl group, a n-hexyl group, a 2-methylpentyl group, a 3-methylpentyl group, a 2,2-dimethylbutyl group, a 2,3-dimethylbutyl group, a n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, a n-octyl group, an isooctyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group.

Examples of the cyclic alkyl group include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group.

Examples of the unsaturated aliphatic group include those obtained by substituting one or more single bonds between adjacent carbon atoms (C—C) in the saturated aliphatic groups with a double bond(s) (C=C) or a triple bond(s) The total number of the double bond(s) (C=C) and the triple bond(s) (C=C) in the unsaturated aliphatic group is preferably smaller, and it is preferably 1 to 3.

The unsaturated aliphatic group is preferably an unsaturated hydrocarbon group. Examples of the unsaturated hydrocarbon group include alkenyl groups and alkynyl groups. More specific examples thereof include those obtained by substituting one single bond between carbon atoms in linear, branched, or cyclic alkyl groups in saturated aliphatic groups with an unsaturated bond (a double bond or a triple bond between carbon atoms).

When the alkenyl group or the alkynyl group in the unsaturated aliphatic group is linear or branched, the number of carbon atoms thereof is preferably 2 to 20, more preferably 2 to 15, particularly preferably 2 to 10. Also, when it is cyclic, the number of carbon atoms thereof is preferably 5 to 10.

The substituent in the aliphatic group which may have a substituent is not particularly limited and may be appropriately selected depending on the intended purpose. Examples thereof include halogen atoms, alkoxy groups, a phenyloxy group, a benzyloxy group, and aromatic groups which may have a substituent. Examples of the halogen atoms include a fluorine atom, a chlorine atom, and a bromine atom. Examples of the alkoxy groups include alkoxy groups containing 1 to 6 carbon atoms. Examples of the aromatic groups which may have a substituent include a phenyl group.

<Aromatic Group which May have a Substituent>

The aromatic group in the aromatic group which may have a substituent represented by the $R^1$, the $R^2$, the $R^3$, and the $R^4$ may have a monocyclic structure or a polycyclic structure. In particular, a phenyl group, a 1-naphthyl group, and a 2-naphthyl group are preferable.

The number of carbon atoms of the aromatic group which may have a substituent is not particularly limited and may be appropriately selected depending on the intended purpose, but is preferably 6 to 15.

The aromatic group is preferably an aromatic hydrocarbon group.

Note that, when the aromatic group which may have a substituent has a substituent, the number of carbon atoms of the aromatic group which may have a substituent refers to the total number of carbon atoms including the number of carbon atoms of the substituent.

The substituent of the aromatic group which may have a substituent is not particularly limited and may be appropriately selected depending on the intended purpose. Examples thereof include halogen atoms, alkoxy groups, and alkyl groups which may have a substituent. Examples of the halogen atoms include a fluorine atom, a chlorine atom, and a bromine atom. Examples of the alkoxy groups include alkoxy groups containing 1 to 6 carbon atoms. Examples of the alkyl groups include alkyl groups containing 1 to 6 carbon atoms. Examples of the substituent in the alkyl groups which may have a substituent include halogen atoms. Examples of the alkyl groups which may have a substituent include a trifluoromethyl group.

The number of the substituents in the aromatic group is not particularly limited and may be appropriately selected depending on the intended purpose. The number of the substituent is, for example, 1 to 4.

The position of the substituents in the aromatic group is not particularly limited and may be appropriately selected depending on the intended purpose, and the substituents may be at an ortho position, a para position, or a meta position.

When a plurality of the substituents bind to the aromatic group, these substituents may be the same substituent or different substituents.

Combinations of the $R^1$ and the $R^2$ are, for example, the following combinations.

(1) Combinations where the $R^1$ is an aromatic group which may have a substituent and the $R^2$ is an aliphatic group which may have a substituent. In these cases, the $R^2$ is preferably an alkyl group containing 1 to 6 carbon atoms.

(2) Combinations where the $R^1$ is an aromatic group which may have a substituent and the $R^2$ is an aromatic group which may have a substituent.

(3) Combinations where the $R^1$ is an aliphatic group which may have a substituent and the $R^2$ is an aromatic group which may have a substituent.

(4) Combinations where the $R^1$ is an aliphatic group which may have a substituent and the $R^2$ is an aliphatic group which may have a substituent. In these cases, the $R^2$ is preferably an alkyl group containing 1 to 6 carbon atoms.

Among them, the combinations of (1) and (4) are preferable.

The compound represented by the General Formula (1) is usually obtained as a mixture of enantiomers. Here, its enantiomeric excess is preferably 80% ee or more, more preferably 90% ee or more.

A method for producing the compound represented by the General Formula (1) is not particularly limited and may be appropriately selected depending on the intended purpose, but is preferably the following production method of the present invention.

(Method for Producing a Compound Represented by General Formula (1))

A method of the present invention for producing a compound is a method for producing a compound represented by the following General Formula (1), and includes a reaction step, and if necessary, further includes other steps.

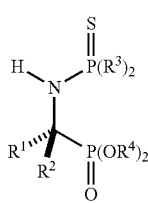

General Formula (1)

In the General Formula (1), $R^1$ and $R^2$ each represent an aliphatic group which may have a substituent, or an aromatic group which may have a substituent (with the proviso that $R^1$ and $R^2$ are different groups), $R^3$ represents an aromatic group which may have a substituent, and $R^4$ represents an aliphatic group which may have a substituent, or an aromatic group which may have a substituent.

Details of the $R^1$, the $R^2$, the $R^3$, and the $R^4$ in the General Formula (1) are as described above relating to the compound represented by the General Formula (1) of the present invention.

<Reaction Step>

The reaction step is a step of reacting a compound represented by the following General Formula (3) and a compound represented by the following General Formula (4).

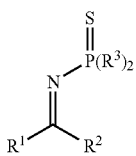

General Formula (3)

In the General Formula (3), $R^1$ and $R^2$ each represent an aliphatic group which may have a substituent, or an aromatic group which may have a substituent (with the proviso that $R^1$ and $R^2$ are different groups), and $R^3$ represents an aromatic group which may have a substituent.

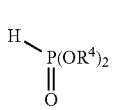

General Formula (4)

In the General Formula (4), $R^4$ represents an aliphatic group which may have a substituent, or an aromatic group which may have a substituent.

Details of the $R^1$, the $R^2$, the $R^3$, and the $R^4$ in the General Formula (3) and the General Formula (4) are the same as those of the $R^1$, the $R^2$, the $R^3$, and the $R^4$ in the General Formula (1).

—Catalyst Containing Asymmetric Ligand—

The reaction step is preferably performed using a catalyst containing an asymmetric ligand.

The catalyst containing an asymmetric ligand is preferably a copper complex containing an asymmetric ligand.

When the catalyst containing an asymmetric ligand is used in the reaction step, the reaction step can be performed with a catalytic amount of a chiral compound without using an expensive chiral compound in a large amount to obtain an optically active compound. Also, when the copper complex containing an asymmetric ligand is used in the reaction step as a catalyst, the compound represented by the General Formula (1) can be produced using inexpensive copper as a catalyst source and with high enantioselectivity. Furthermore, after completion of the reaction step, the asymmetric ligand can be recovered.

The asymmetric ligand in the copper complex containing an asymmetric ligand is not particularly limited and may be appropriately selected depending on the intended purpose, but is preferably an optically active phosphine ligand from the viewpoint of being excellent in enantioselectivity. That is, the copper complex containing an asymmetric ligand is preferably a copper-optically active phosphine complex. The copper-optically active phosphine complex is a complex of copper and an optically active phosphine ligand.

The optically active phosphine ligand is not particularly limited and may be appropriately selected depending on the intended purpose. Examples thereof include cyclohexylanisylmethylphosphine (CAMP), 1,2-bis(anisylphenylphosphino)ethane (DIPAMP), 1,2-bis(alkylmethylphosphino)ethane (BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis(diphenylphosphino)butane (DIOP), 1-cyclohexyl-1,2-bis(diphenylphosphino)ethane (CYCPHOS), 1-substituted-3,4-bis(diphenylphosphino)pyrrolidine (DEGPHOS), 2,4-bis(diphenylphosphino)pentane (SKEWPHOS), 1,2-bis(substituted phosphorano)benzene (DuPHOS), 1,2-bis(substituted phosphorano)ethane (BPE), 1-(substituted phosphorano)-2-(diphenylphosphino)benzene (UCAP-Ph), 1-(bis(3,5-dimethylphenyl)phosphino)-2-(substituted phosphorano)benzene (UCAP-DM), 1-(substituted phosphorano)-2-(bis(3,5-di(tert-butyl)-4-methoxyphenyl)phosphino)benzene (UCAP-DTBM), 1-(substituted phosphorano)-2-(di-naphtnalen-1-yl-phosphino)benzene (UCAP-(1-Nap)), 1-[1',2-bis(diphenylphosphino)ferrocenyl]ethylamine (BPPFA), 1-[1',2-bis(diphenylphosphino)ferrocenyl]ethyl alcohol (BPPFOH), 2,2'-bis(diphenylphosphino)-1,1'-dicyclopentane (BICP), 2,2'-bis(diphenylphosphino)-1,1'-binaphthyl (BINAP), 2,2'-bis(diphenylphosphino)-1,1'-(5,5',6,6',7,7',8,8',-octahydrobinaphthyl) ($H_8$-BINAP), 2,2'-bis(di-p-tolylphosphino)-1,1'-binaphthyl (TOL-BINAP), 2,2'-bis(di(3,5-dimethylphenyl)phosphino)-1,1'-binaphthyl) (DM-BINAP), 2,2'-bis(diphenylphosphino)-6,6'-dimethyl-1,1'-biphenyl (BICHEP), ((5,6),(5',6')-bis(methylenedioxy)biphenyl-2,2'-diyl) (bisdiphenylphosphine) (SEGPHOS), ((5,6),(5',6')-bis(methylenedioxy)biphenyl-2,2'-diyl) (bis(3,5-dimethylphenyl)phosphine) (DM-SEGPHOS), and ((5,6),(5',6')-bis(methylenedioxy)biphenyl-2,2'-diyl) (bis(3,5-di(tert-butyl)-4-methoxyphenyl)phosphine) (DTBM-SEGPHOS).

Among them, the optically active phosphine ligand is preferably (R,R)-2,5 substituted-BPE, more preferably (R,R)-Ph-BPE, from the viewpoint of being more excellent in enantioselectivity.

Note that, (R,R)-Ph-BPE is a compound expressed by the following structural formula:

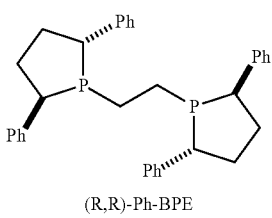 [SMILES: c1ccc([C@H]2CC[C@H](c3ccccc3)P2CCP2[C@@H](c3ccccc3)CC[C@@H]2c2ccccc2)cc1]

(R,R)-Ph-BPE where "Ph" denotes a phenyl group.

An amount of the catalyst containing an asymmetric ligand used in the reaction step is not particularly limited and may be appropriately selected depending on the intended purpose, but is preferably 0.1 mol % to 5 mol %, more preferably 0.3 mol % to 3 mol %, particularly preferably 0.5 mol % to 1 mol %, relative to the compound represented by the General Formula (3).

In the reaction step, a base is preferably used together with the catalyst containing an asymmetric ligand. The base may be an organic base or an inorganic base, but is preferably an inorganic base because it is inexpensive and easy to handle. Examples of the organic base include triethylamine. Examples of the inorganic base include potassium carbonate.

An amount of the base used is not particularly limited and may be appropriately selected depending on the intended purpose.

A ratio between the compound represented by the General Formula (3) and the compound represented by the General Formula (4) in the reaction step is not particularly limited and may be appropriately selected depending on the intended purpose. The ratio of the compound represented by the General Formula (4) is preferably 1.0 equivalent to 3.0 equivalents relative to the compound represented by the General Formula (3).

A solvent used in the reaction step is not particularly limited and may be appropriately selected depending on the intended purpose. Examples thereof include THF (tetrahydrofuran) and DMF (N,N-dimethylformamide). These may used alone or in combination.

The reaction step is preferably performed in the absence of a solvent from the viewpoints of reducing the cost for the solvent and reducing the volume of a reaction container.

In the reaction step, the reaction proceeds under mild conditions. Thus, the reaction step can be performed without controlling the reaction temperature. The reaction step therefore can be performed at, for example, normal temperature. The normal temperature is, for example, 20° C. to 30° C.

The reaction time in the reaction step is not particularly limited and may be appropriately selected depending on the intended purpose, but is preferably 24 hours to 100 hours, more preferably 48 hours to 96 hours.

The method of the present invention for producing the compound represented by the General Formula (1) does not yield any by-products in addition to the compound represented by the General Formula (1) as a product through reaction between the compound represented by the General Formula (3) and the compound represented by the General Formula (4). In this method, therefore, it is easy to reuse the solvent used in the reaction, which is very excellent in terms of green chemistry as well.

(Method for Producing Optically Active α-Aminophosphonic Acid Derivative)

A method of the present invention for producing an optically active α-aminophosphonic acid derivative includes a conversion step, and if necessary, further includes other steps.

<Conversion Step>

The conversion step is a step of converting a compound represented by the following General Formula (1) to an optically active α-aminophosphonic acid derivative represented by the following General Formula (2).

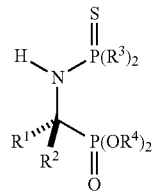

General Formula (1)

In the General Formula (1), $R^1$ and $R^2$ each represent an aliphatic group which may have a substituent, or an aromatic group which may have a substituent (with the proviso that $R^1$ and $R^2$ are different groups), $R^3$ represents an aromatic group which may have a substituent, and $R^4$ represents an aliphatic group which may have a substituent, or an aromatic group which may have a substituent.

Details of the $R^1$, the $R^2$, the $R^3$, and the $R^4$ in the General Formula (1) are as described above relating to the compound represented by the General Formula (1) of the present invention.

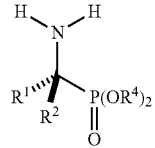

General Formula (2)

In the General Formula (2), $R^1$ and $R^2$ each represent an aliphatic group which may have a substituent, or an aromatic group which may have a substituent (with the proviso that $R^1$ and $R^2$ are different groups), and $R^4$ represents an aliphatic group which may have a substituent, or an aromatic group which may have a substituent.

Details of the $R^1$, the $R^2$, and the $R^4$ in the General Formula (2) are the same as those of the $R^1$, the $R^2$, and the $R^4$ in the General Formula (1).

The conversion step is, for example, a step of heating the compound represented by the General Formula (1) under acidic conditions, to thereby convert a $-P(=S)(R^3)_2$ group binding to the nitrogen atom in the compound represented by the General Formula (1) to a hydrogen atom. Examples of reagents for making the reaction system acidic conditions include perchloric acid and hydrochloric acid.

The conversion step can be performed in the presence of a solvent. Examples of the solvent include alcohols. Examples of the alcohols include ethanol and isopropyl alcohol.

The heating temperature in the conversion step is not particularly limited and may be appropriately selected depending on the intended purpose, and is, for example, 50° C. to 90° C.

The reaction time in the conversion step is not particularly limited and may be appropriately selected depending on the intended purpose, and is, for example, 1 hour to 5 hours.

(Optically Active α-Aminophosphonic Acid Derivative)

An optically active α-aminophosphonic acid derivative of the present invention is represented by the following General Formula (2).

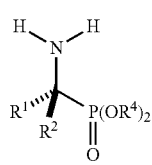

General Formula (2)

In the General Formula (2), $R^1$ and $R^2$ each represent an aliphatic group which may have a substituent, or an aromatic group which may have a substituent (with the proviso that $R^1$ and $R^2$ are different groups), and $R^4$ represents an aliphatic group which may have a substituent, or an aromatic group which may have a substituent (with the proviso that when the $R^4$ is the aromatic group which may have a substituent, the $R^4$ is the aliphatic group which may have a substituent).

Details of the $R^1$, the $R^2$, and the $R^4$ in the General Formula (2) are as described above relating to the compound represented by the General Formula (1) of the present invention.

An enantiomeric excess (optical purity) of the optically active α-aminophosphonic acid derivative represented by the General Formula (2) is preferably 80% ee or more, more preferably 85% ee or more, further preferably 90% ee or more, particularly preferably 95% ee or more. A method for obtaining the optically active α-aminophosphonic acid derivative represented by the General Formula (2) with high enantiomeric excess is not particularly limited and may be appropriately selected depending on the intended purpose. It is preferably a method which combines the method of the present invention for producing the compound represented by the General Formula (1), with the method of the present invention for producing the optically active α-aminophosphonic acid derivative represented by the General Formula (2).

The enantiomeric excess (optical purity) can be measured by, for example, HPLC (high-performance liquid chromatography).

EXAMPLES

The present invention will next be described in detail by way of Examples of the present invention. The present invention, however, should not be construed as being limited to the Examples.

Note that, in the following Examples, "Me" denotes "methyl group", "Et" denotes "ethyl group", "Ph" denotes "phenyl group", "Bn" denotes "benzyl group", and "THF" denotes "tetrahydrofuran".

Synthesis Example 1

Synthesis of Copper Complex Containing an Asymmetric Ligand (Copper-Optically Active Phosphine Complex)

A magnetic stirrer was added to a 20-mL test tube, which was then dried with heating. [Cu(CH$_3$CN)$_4$]PF$_6$ (3.7 mg, 0.01 mmol, product of Sigma-Aldrich Co.) and (R,R)-Ph-BPE (5.1 mg, 0.01 mmol, product of Sigma-Aldrich Co.) were charged to the 20-mL test tube in an Ar atmosphere. Dry THF (2.0 mL) was added thereto, and the mixture was stirred at room temperature for 1 hour. Et$_3$N (70 μL, 0.50 mmol) was added to the mixture to obtain a colorless, transparent catalyst solution (copper complex 0.005 M; Et$_3$N 0.25 M).

Synthesis Example 2

Synthesis of Thiophosphinoyl Ketimine

Each of the thiophosphinoyl ketimines (the compounds represented by the General Formula (3)) used in the following Examples 1 to 18 was synthesized in accordance with Xinyuan Xu, et al., Heteroatom Chemistry, Volume 19, Number 3, 2008.

Example 1

A magnetic stirrer was added to a 20-mL test tube, which was then dried with heating. Thiophosphinoyl ketimine (the compound represented by the General Formula (3) where $R^1$ is a phenyl group, $R^2$ is a methyl group, and $R^3$ is a phenyl group; 67.0 mg, 0.2 mmol) was added to the 20-mL test tube, which was placed in an Ar atmosphere. Subsequently, 0.2 mL of the catalyst solution obtained in Synthesis Example 1 (copper complex 0.001 mmol, Et$_3$N 0.05 mmol) was added thereto at room temperature. Diethyl phosphonate (51.6 μL, 0.4 mmol) was added thereto, followed by stirring at room temperature for 72 hours. The reaction mixture was purified by fraction thin-layer chromatography (silica gel plate, hexane/ethyl acetate=1/1 (v/v)) to obtain a product expressed by the following structural formula (entry 1) (85.2 mg, 90% yield, 96% ee).

The optical purity was determined by HPLC. Details of HPLC are as follows.
Column: CHIRALPAK IA (0.46 cm in diameter×25 cm)
Solvent: isopropyl alcohol/hexane=1/9 (v/v)
Flow rate: 1.0 mL/min
Detection wavelength: 254 nm
Retention time: 8.9 min (minor), 11.2 min (major)

A $^1$H-NMR spectrum of the obtained product is shown below.

<Entry 1>

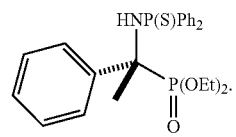

1

$^1$H NMR (CDCl$_3$): δ 8.19-8.14 (m, 2H), 7.83-7.77 (m, 2H), 7.56-7.40 (m, 6H), 7.38-7.27 (m, 5H), 4.13-4.03 (m, 2H), 3.92 (t, J=7.6 Hz, 1H), 3.83-3.77 (m, 1H), 3.53-3.47 (m, 1H), 1.96 (d, J=17.4 Hz, 3H), 1.30 (t, J=7.1 Hz, 3H), 1.08 (t, J=7.1 Hz, 3H).

Examples 2 to 18

Synthesis was performed in the same manner as in Example 1, except that in Example 1, the kind of thiophosphinoyl ketimine, the kind of the phosphorous acid diester, and the amount of the copper complex were changed to the kind of thiophosphinoyl ketimine, the kind of the phosphorous acid diester, and the amount of the copper complex described in the following Table 1.

The obtained product was determined for yield (%) and enantiomeric excess (% ee) in the same manner as in Example 1. The results are shown in Table 1. Also, the obtained product was subjected to $^1$H-NMR measurement. The results are shown below.

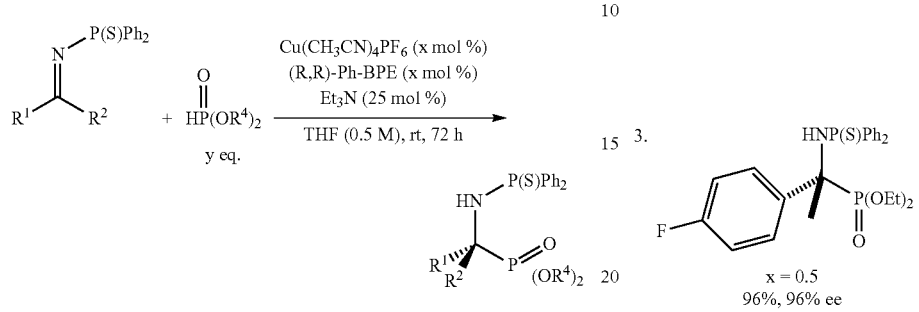

TABLE 1

| Example | entry | substrate R$^1$ | R$^2$ | R$^4$ | y (eq.) | x (mol %) | yield (%) | ee (%) |
|---|---|---|---|---|---|---|---|---|
| 1 | 1 | C$_6$H$_5$ | Me | Et | 2 | 0.5 | 90 | 96 |
| 2 | 2 | 4-CF$_3$—C$_6$H$_4$ | Me | Et | 2 | 0.5 | 97 | 96 |
| 3 | 3 | 4-F—C$_6$H$_4$ | Me | Et | 2 | 0.5 | 96 | 96 |
| 4 | 4 | 4-Cl—C$_6$H$_4$ | Me | Et | 2 | 0.5 | 90 | 94 |
| 5 | 5 | 4-Br—C$_6$H$_4$ | Me | Et | 2 | 0.5 | 94 | 97 |
| 6 | 6 | 3-Br—C$_6$H$_4$ | Me | Et | 2 | 0.5 | 94 | 95 |
| 7 | 7 | 2-F—C$_6$H$_4$ | Me | Et | 2 | 0.5 | 93 | 96 |
| 8 | 8 | 4-Me—C$_6$H$_4$ | Me | Et | 2 | 2 | 97 | 94 |
| 9 | 9 | 3-Me—C$_6$H$_4$ | Me | Et | 2 | 2 | 94 | 97 |
| 10 | 10 | 4-MeO—C$_6$H$_4$ | Me | Et | 2 | 2 | 68 | 97 |
| 11 | 11 | 3-MeO—C$_6$H$_4$ | Me | Et | 2 | 1 | 71 | 97 |
| 12 | 12 | cyclohexyl | Me | Et | 3 | 1 | 95 | 95 |
| 13 | 13 | PhCH$_2$CH$_2$ | Me | Et | 3 | 1 | 96 | 90 |
| 14 | 14 | (CH$_3$)$_2$CHCH$_2$ | Me | Et | 3 | 1 | 90 | 94 |
| 15 | 15 | (CH$_3$)$_2$CH═CH(CH$_2$)$_2$ | Me | Et | 3 | 1 | 93 | 86 |
| 16 | 16 | C$_6$H$_5$ | Me | Me | 2 | 0.5 | 97 | 95 |
| 17 | 17 | C$_6$H$_5$ | Me | Bn | 2 | 1 | 93 | 97 |
| 18 | 18 | C$_6$H$_5$ | Et | Et | 2 | 2 | 86 | 89 |

In the Table 1 and the reaction formula, "x" denotes mol % of the copper complex relative to 1 mol of the thiophosphinoyl ketimine (the compound represented by the General Formula (3)), and "y" denotes an equivalent of the phosphorous acid diester relative to 1 mol of the thiophosphinoyl ketimine (the compound represented by the General Formula (3)).

The structures of the compounds obtained in Examples 1 to 18 are shown below. The percentile values below each structural formula are yield (%) and enantiomeric excess (% ee) of each compound.

-continued
6. 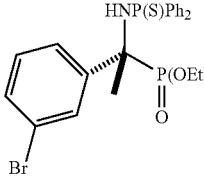
x = 0.5
94%, 95% ee
7. 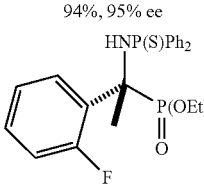
x = 0.5
93%, 96% ee
8. 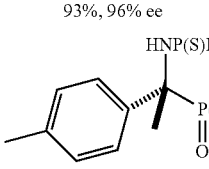
x = 2
97%, 94% ee
9. 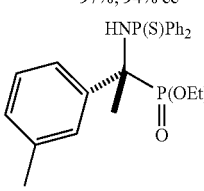
x = 2
94%, 97% ee
10. 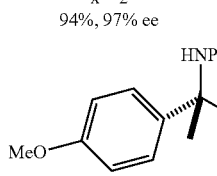
x = 2
68%, 97% ee
11. 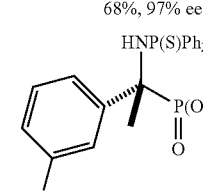
x = 1
71%, 97% ee
12. 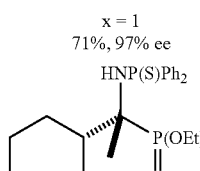
x = 1
95%, 95% ee
13. 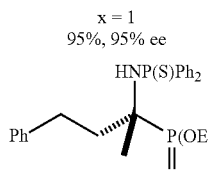
x = 1
96%, 90% ee
-continued
14. 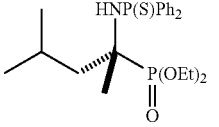
x = 1
90%, 94% ee
15. 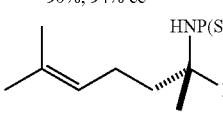
x = 1
93%, 86% ee
16. 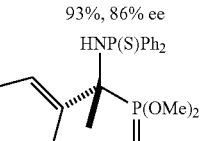
x = 0.5
97%, 95% ee
17. 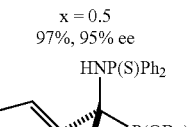
x = 1
93%, 97% ee
18. 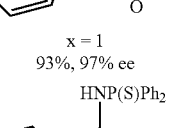
x = 1
86%, 89% ee
<Entry 2>
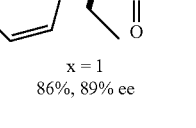
$^1$H NMR (CDCl$_3$): δ 8.19-8.13 (m, 2H), 7.82-7.77 (m, 2H), 7.69 (dd, J=2.1, 8.2 Hz, 2H), 7.58 (d, J=8.7 Hz, 2H), 7.50-7.42 (m, 4H), 7.40-7.36 (m, 2H), 4.12-4.04 (m, 2H), 3.94-3.83 (m, 2H), 3.69-3.59 (m, 1H), 1.98 (d, J=17.2 Hz, 3H), 1.29 (t, J=7.1 Hz, 3H), 1.12 (t, J=7.1 Hz, 3H).
<Entry 3>
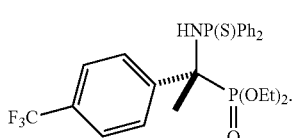
$^1$H NMR (CDCl$_3$): δ 8.11 (dd, J=8.0, 13.7 Hz, 2H), 7.75 (dd, J=8.0, 13.7 Hz, 2H), 7.49-7.29 (m, 8H), 6.96 (t, J=8.4

Hz, 2H), 4.06-4.00 (m, 2H), 3.83-3.76 (m, 2H), 3.56-3.49 (m, 1H), 1.89 (d, J=17.1 Hz, 3H), 1.25 (t, J=7.1 Hz, 3H), 1.06 (t, J=7.1 Hz, 3H).

<Entry 4>

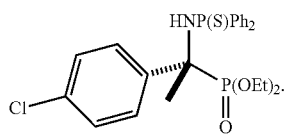

4

¹H NMR (CDCl₃): δ 8.18-8.12 (m, 2H), 7.82-7.76 (m, 2H), 7.50-7.37 (m, 8H), 7.29 (d, J=8.7 Hz, 2H), 4.12-4.04 (m, 2H), 3.90-3.81 (m, 2H), 3.63-3.57 (m, 1H), 1.93 (d, J=17.2 Hz, 3H), 1.30 (t, J=7.1 Hz, 3H), 1.12 (t, J=7.1 Hz, 3H).

<Entry 5>

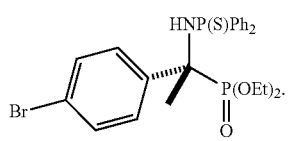

5

¹H NMR (CDCl₃): δ 8.16 (dd, J=8.0, 13.7 Hz, 2H), 7.80 (dd, J=8.0, 13.7 Hz, 2H), 7.51-7.35 (m, 10H), 4.12-4.04 (m, 2H), 3.89-3.81 (m, 2H), 3.64-3.58 (m, 1H), 1.93 (d, J=17.4 Hz, 3H), 1.30 (t, J=7.1 Hz, 3H), 1.12 (t, J=7.1 Hz, 3H).

<Entry 6>

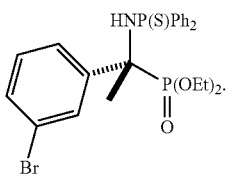

6

¹H NMR (CDCl₃): δ 8.27-8.14 (m, 2H), 7.84-7.79 (m, 2H), 7.67 (d, J=1.6 Hz, 1H), 7.54-7.40 (m, 8H), 7.27-7.22 (m, 1H), 4.16-4.09 (m, 2H), 3.92-3.86 (m, 2H), 3.68-3.62 (m, 1H), 1.97 (d, J=17.2 Hz, 3H), 1.34 (t, J=7.1 Hz, 3H), 1.16 (t, J=7.1 Hz, 3H).

<Entry 7>

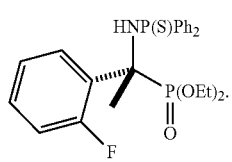

7

¹H NMR (CDCl₃): δ 8.19-8.12 (m, 2H), 7.75-7.70 (m, 2H), 7.46-7.23 (m, 8H), 7.09-6.97 (m, 2H), 4.23 (q, J=12.2, 1H), 4.14-4.02 (m, 2H), 3.91-3.81 (m, 1H), 3.69-3.62 (m, 1H), 1.93 (d, J=16.9 Hz, 3H), 1.26 (t, J=7.1 Hz, 3H), 1.07 (t, J=7.1 Hz, 3H).

<Entry 8>

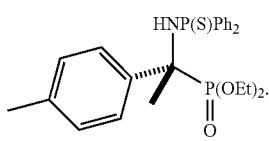

8

¹H NMR (CDCl₃): δ 8.20-8.14 (m, 2H), 7.83-7.78 (m, 2H), 7.52-7.40 (m, 6H), 7.38-7.35 (m, 2H), 7.13 (d, J=8.5 Hz, 2H), 4.14-4.00 (m, 2H), 3.89-3.76 (m, 2H), 3.58-3.48 (m, 1H), 2.32 (d, J=1.8 Hz, 3H), 1.94 (d, J=17.4 Hz, 3H), 1.30 (t, J=7.2 Hz, 3H), 1.10 (t, J=7.1 Hz, 3H).

<Entry 9>

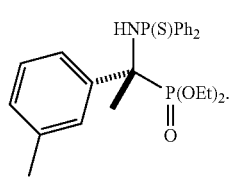

9

¹H NMR (CDCl₃): δ 8.18-8.12 (m, 2H), 7.82-7.77 (m, 2H), 7.48-7.42 (m, 4H), 7.36-7.31 (m, 4H), 7.22 (t, J=7.8 Hz, 1H), 7.08 (d, J=7.3 Hz, 1H), 4.11-4.02 (m, 2H), 3.89-3.78 (m, 2H), 3.54-3.50 (m, 1H), 2.32 (s, 3H), 1.95 (d, J=17.4 Hz, 3H), 1.30 (t, J=7.1 Hz, 3H), 1.09 (t, J=7.1 Hz, 3H).

<Entry 10>

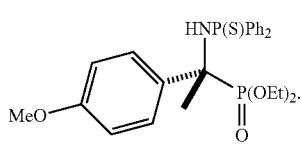

10

¹H NMR (CDCl₃): δ 8.18-8.13 (m, 2H), 7.82-7.77 (m, 2H), 7.46-7.34 (m, 8H), 6.87-6.83 (m, 2H), 4.11-4.01 (m, 2H), 3.86-3.79 (m, 2H), 3.78 (s, 3H), 3.56-3.50 (m, 1H), 1.93 (d, J=17.4 Hz, 3H), 1.30 (t, J=7.1 Hz, 3H), 1.10 (t, J=7.1 Hz, 3H).

<Entry 11>

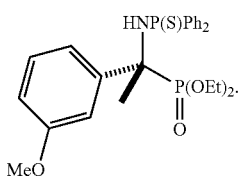

11

¹H NMR (CDCl₃): δ 8.18-8.13 (m, 2H), 7.84-7.78 (m, 2H), 7.47-7.34 (m, 6H), 7.24 (t, J=8.0 Hz, 1H), 7.16-7.10 (m, 2H), 6.83-6.80 (m, 1H), 4.10-4.04 (m, 2H), 3.87-3.81 (m, 2H), 3.77 (s, 3H), 3.60-3.54 (m, 1H), 1.94 (d, J=17.2 Hz, 3H), 1.29 (t, J=7.1 Hz, 3H), 1.10 (1, J=7.1 Hz, 3H).

<Entry 12>

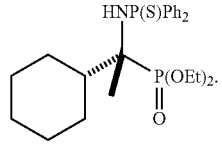

¹H NMR (CDCl₃): δ 8.22-8.17 (m, 2H), 7.91-7.86 (m, 2H), 7.45-7.40 (m, 6H), 4.16-4.04 (m, 4H), 3.21 (t, J=5.7 Hz, 1H), 2.31-2.18 (m, 1H), 1.96-1.61 (m, 5H), 1.49 (d, J=17.6 Hz, 3H), 1.42-1.10 (m, 11H).

<Entry 13>

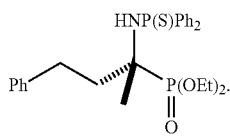

¹H NMR (CDCl₃): δ 8.23-8.18 (m, 2H), 7.95-7.90 (m, 2H), 7.47-7.39 (m, 6H), 7.26-7.24 (m, 4H), 7.15-7.12 (m, 1H), 4.27-4.14 (m, 4H), 3.12-3.10 (m, 1H), 2.94-2.85 (m, 2H), 2.69-2.53 (m, 1H), 2.22-2.11 (m, 1H), 1.53 (d, J=17.2 Hz, 3H), 1.39-1.32 (m, 6H).

<Entry 14>

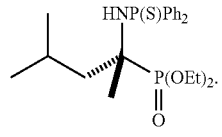

¹H NMR (CDCl₃): δ 8.21-8.16 (m, 2H), 7.95-7.89 (m, 2H), 7.44-7.36 (m, 6H), 4.21-4.07 (m, 4H), 2.99 (t, J=5.0 Hz, 1H), 2.14-2.03 (m, 2H), 1.93-1.86 (m, 1H), 1.53 (d, J=17.6 Hz, 3H), 1.35-1.29 (m, 6H), 0.98 (d, J=6.4 Hz, 3H), 0.93 (d, J=6.4 Hz, 3H).

<Entry 15>

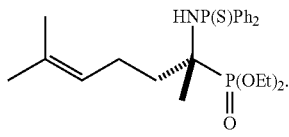

¹H NMR (CDCl₃): δ 8.21-8.15 (m, 2H), 7.95-7.89 (m, 2H), 7.45-7.38 (m, 6H), 5.12-5.09 (m, 1H), 4.20-4.11 (m, 4H), 3.06 (t, J=4.8 Hz, 1H), 2.31-2.14 (m, 3H), 1.95-1.84 (m, 1H), 1.58 (d, J=8.7 Hz, 6H), 1.50 (d, J=7.2 Hz, 3H), 1.34 (d, J=7.1 Hz, 3H), 1.32 (t, J=7.1 Hz, 3H).

<Entry 16>

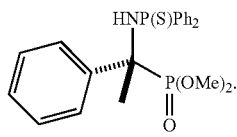

¹H NMR (CDCl₃): δ 8.17-8.11 (m, 2H), 7.83-7.78 (m, 2H), 7.57-7.54 (m, 2H), 7.49-7.40 (m, 4H), 7.37-7.26 (m, 5H), 3.90 (t, J=7.6 Hz, 1H), 3.74 (d, J=10.3 Hz, 3H), 3.36 (d, J=10.3 Hz, 3H), 1.96 (d, J=17.6 Hz, 3H).

<Entry 17>

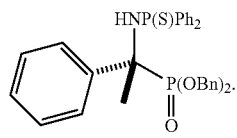

¹H NMR (CDCl₃): δ 8.02 (dd, J=7.4, 13.8 Hz, 2H), 7.76 (dd, J=7.4, 13.8 Hz, 2H), 7.57 (dd, J=2.0, 7.6 Hz, 2H), 7.43-7.22 (m, 17H), 7.13-7.09 (m, 2H), 5.01 (dd, J=8.7, 11.7 Hz, 1H), 4.91 (dd, J=6.7, 11.7 Hz, 1H), 4.70 (dd, J=6.7, 11.7 Hz, 1H), 4.36 (dd, J=8.5, 11.7 Hz, 1H), 3.93 (t, J=7.3 Hz, 1H), 1.98 (d, J=17.6 Hz, 3H).

<Entry 18>

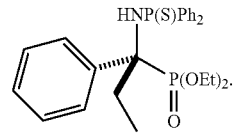

¹H NMR (CDCl₃): δ 8.14-8.09 (m, 2H), 7.92-7.87 (m, 2H), 7.70-7.68 (m, 2H), 7.45-7.35 (m, 6H), 7.28-7.21 (m, 3H), 3.99-3.91 (m, 2H), 3.88-3.83 (m, 2H), 3.66 (q, J=8.9 Hz, 1H), 2.80-2.69 (m, 1H), 2.50-2.40 (m, 1H), 1.21-1.14 (m, 6H), J=7.3 Hz, 3H).

Example 19

The compound of entry 1 (47.3 mg, 0.1 mmol) obtained in Example 1, ethanol (0.5 mL), and HClO₄ (aqueous solution (60% by mass), 0.1 mL) were added to a 20-mL test tube, followed by stirring at 80° C. for 2 hours. The reaction mixture was cooled to room temperature, and saturated aqueous solution of sodium hydrogen carbonate was added thereto. The mixture was extracted with ethyl acetate, and the organic layer was dried with anhydrous sodium hydrogen carbonate. The residue obtained by concentration under reduced pressure was purified by fraction thin-layer chromatography (ethyl acetate/MeOH/Et₃N=10/1/0.1 (v/v/v)) to obtain an amine compound expressed by the following structural formula (viscous oily matter, 19.3 mg, yield 75%).

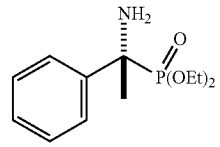

The obtained product was subjected to ¹H-NMR measurement. The results are shown below.

¹H NMR (CDCl₃): δ 7.60 (dd, J=2.2, 7.8 Hz, 2H); 7.33 (t, J=7.6 Hz, 2H); 7.27-7.22 (m, 1H); 4.03-3.85 (m, 3H); 3.81-3.72 (m, 1H), 1.92 (br, 2H); 1.70 (d, J=15.8 Hz, 3H), 1.23 (t, J=7.1 Hz, 3H); 1.12 (t, J=7.1 Hz, 3H)

Example 20

The compound of entry 4 (65 mg, 0.128 mmol) obtained in Example 4, ethanol (1.0 mL), and HClO₄ (aqueous solution (60% by mass), 0.2 mL) were added to a 20-mL test tube, followed by stirring at 80° C. overnight. The reaction mixture was cooled to room temperature, and saturated aqueous solution of sodium hydrogen carbonate was added thereto. The mixture was extracted with ethyl acetate, and the organic layer was dried with anhydrous sodium hydrogen carbonate. The residue obtained by concentration under reduced pressure was purified by fraction thin-layer chromatography (CH₂Cl₂→CH₂Cl₂/MeOH=20/1 (v/v)) to obtain an amine compound expressed by the following structural formula (oily matter, 30.2 mg, yield 81%).

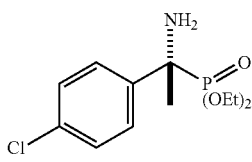

The obtained product was subjected to ¹H-NMR measurement. The results are shown below.

¹H NMR (CDCl₃): δ 7.56-7.53 (m, 2H), 7.30 (d, J=7.8 Hz, 2H), 4.10-3.98 (m, 2H), 3.96-3.88 (m, 1H), 3.85-3.75 (m, 1H), 1.86 (br, 2H), 1.66 (d, J=15.8 Hz, 3H), 1.25 (td, J=7.1, 1.6 Hz, 3H), 1.15 (td, J=7.1, 1.4 Hz, 3H)

Example 21

The compound of entry 13 (42 mg, 0.084 mmol) obtained in Example 13, ethanol (1.0 mL), and HClO₄ (aqueous solution (60% by mass), 0.2 mL) were added to a 20-mL test tube, followed by stirring at 80° C. overnight. The reaction mixture was cooled to room temperature, and saturated aqueous solution of sodium hydrogen carbonate was added thereto. The mixture was extracted with ethyl acetate, and the organic layer was dried with anhydrous sodium hydrogen carbonate. The residue obtained by concentration under reduced pressure was purified by fraction thin-layer chromatography (CH₂Cl₂→CH₂Cl₂/MeOH=20/1 (v/v)) to obtain an amine compound expressed by the following structural formula (oily matter, 21.2 mg, yield 89%).

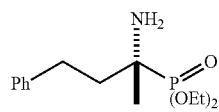

The obtained product was subjected to ¹H-NMR measurement. The results are shown below.

¹H NMR (CDCl₃): δ 7.28-7.24 (m, 2H), 7.19-7.14 (m, 3H), 4.18-4.10 (m, 4H), 2.86-2.78 (m, 1H), 2.73-2.66 (m, 1H), 1.93-1.85 (m, 2H), 1.66 (br, 2H), 1.35-1.30 (m, 9H)

Example 22

Recovery and Reuse of Catalyst

A magnetic stirrer was added to a 50-mL recovery flask, which was then dried with heating. [Cu(CH₃CN)₄]PF₆ (11.2 mg, 0.03 mmol, product of Sigma-Aldrich Co.) and (R,R)-Ph-BPE (15.2 mg, 0.03 mmol, product of Sigma-Aldrich Co.) were charged to the 50-mL test tube in an Ar atmosphere. Dry THF (6.0 mL) was added thereto, and the mixture was stirred at room temperature for 1 hour. Thiophosphinoyl ketimine (the compound represented by the General Formula (3) where R¹ is a phenyl group, R² is a methyl group, and R³ is a phenyl group; 1.0 g, 3 mmol) and Et₃N (104 μL, 0.75 mmol) were added thereto, followed by stirring at room temperature for 10 minutes. Diethyl phosphonate (774 μL, 6 mmol) was added thereto, followed by stirring at room temperature for 72 hours in an Ar atmosphere. Thereafter, neutral silica gel (4 mL) was added to the reaction mixture, and the solvent was evaporated under reduced pressure. The residue was purified by silica gel column chromatography (neutral silica gel, hexane/ethyl acetate=4/1 to 1/1 (v/v)) to obtain a product expressed by the following structural formula (1.29 g, 91% yield, 91% ee).

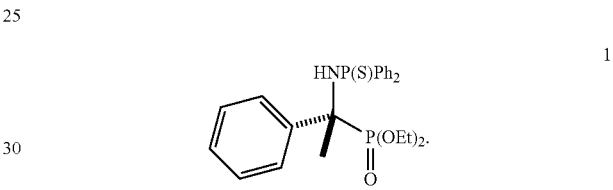

The optical purity was determined by HPLC. Details of HPLC are as follows.
Column: CHIRALPAK IA (0.46 cm in diameter×25 cm)
Solvent: isopropyl alcohol/hexane=1/9 (v/v)
Flow rate: 1.0 mL/min
Detection wavelength: 254 nm
Retention time: 8.9 min (minor), 11.2 min (major)

CH₂Cl₂/CH₃CN=3/1 (v/v) was used as an elution solvent of the silica gel column to elute Cu/(R,R)-Ph-BPE (complex), which was obtained as white powder. The obtained complex was dissolved in 6 mL of THF, and 600 μL of the solution was added to a dried 20-mL test tube containing thiophosphinoyl ketimine (the compound represented by the General Formula (3) where R¹ is a phenyl group, R² is a methyl group, and R³ is a phenyl group; 100 mg, 0.3 mmol), and then Et₃N (10.4 μL, 0.075 mmol) was added thereto, followed by stirring at room temperature for 10 minutes. Diethyl phosphonate (77.4 μmL, 0.6 mmol) was added thereto, followed by stirring at room temperature for 72 hours in an Ar atmosphere. The reaction mixture was purified by fraction thin-layer chromatography (silica gel plate, hexane/ethyl acetate=1/1 (v/v)) to obtain a product expressed by the following structural formula (126 mg, 89% yield, 95% ee). Its optical purity was determined under the same conditions as the above-described HPLC.

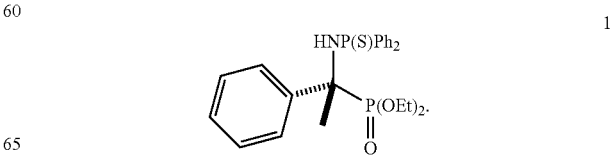

On the basis of the above, it could be confirmed that the catalyst could be recovered and reused.

Example 23

Reaction in the Absence of Solvent

A magnetic stirrer was added to a 20-mL test tube, which was then dried with heating. Thiophosphinoyl ketimine (the compound represented by the General Formula (3) where $R^1$ is a phenyl group, $R^2$ is a methyl group, and $R^3$ is a phenyl group; 9.3 mg, 0.25 mmol), $[Cu(CH_3CN)_4]PF_6$ (0.9 mg, 0.0025 mmol, product of Sigma-Aldrich Co.), (R,R)-Ph-BPE (1.3 mg, 0.0025 mmol, product of Sigma-Aldrich Co.), and diethyl phosphonate (51.6 μmL, 0.4 mmol) were added to the 20-mL test tube, followed by stirring for 30 minutes in an Ar atmosphere. Then, $Et_3N$ (8.7 μL, 0.0625 mmol) was added thereto. The mixture was stirred at room temperature for 5 days, and the reaction mixture was purified by fraction thin-layer chromatography (silica gel plate, hexane/ethyl acetate=1/1 (v/v)) to obtain a product expressed by the following structural formula (106.5 mg, 90% yield, 93% ee).

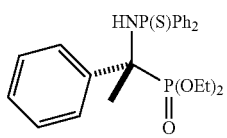

Example 24

Reaction Using Inorganic Base

A magnetic stirrer was added to a 20-mL test tube, which was then dried with heating. Thiophosphinoyl ketimine (the compound represented by the General Formula (3) where $R^1$ is a phenyl group, $R^2$ is a methyl group, and $R^3$ is a phenyl group; 33.5 mg, 0.1 mmol), $[Cu(CH_3CN)_4]PF_6$ (1.8 mg, 0.005 mmol, product of Sigma-Aldrich Co.), (R,R)-Ph-BPE (2.6 mg, 0.005 mmol, product of Sigma-Aldrich Co.), and THF (0.2 mL) were added to the 20-mL test tube. Potassium carbonate (6.9 mg, 0.05 mmol) and diethyl phosphonate (25.8 μL, 0.2 mmol) were added thereto, followed by stirring at room temperature for 12 days. The reaction mixture was purified by fraction thin-layer chromatography (silica gel plate, hexane/ethyl acetate=1/1 (v/v)) to obtain a product expressed by the following structural formula (46.9 mg, 99% yield, 96% ee).

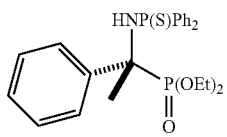

Aspects of the present invention are, for example, as follows.

<1> A method for producing an optically active α-aminophosphonic acid derivative, the method including:
converting a compound represented by the following General Formula (1) to an optically active α-aminophosphonic acid derivative represented by the following General Formula (2):

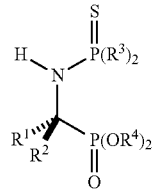

General Formula (1)

where in the General Formula (1), $R^1$ and $R^2$ each represent an aliphatic group which may have a substituent, or an aromatic group which may have a substituent (with the proviso that $R^1$ and $R^2$ are different groups), $R^3$ represents an aromatic group which may have a substituent, and $R^4$ represents an aliphatic group which may have a substituent, or an aromatic group which may have a substituent,

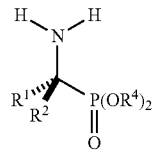

General Formula (2)

where in the General Formula (2), $R^1$ and $R^2$ each represent an aliphatic group which may have a substituent, or an aromatic group which may have a substituent (with the proviso that $R^1$ and $R^2$ are different groups), and $R^4$ represents an aliphatic group which may have a substituent, or an aromatic group which may have a substituent.

<2> An optically active α-aminophosphonic acid derivative represented by the following General Formula (2):

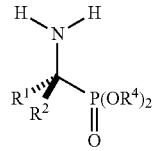

General Formula (2)

where in the General Formula (2), $R^1$ and $R^2$ each represent an aliphatic group which may have a substituent, or an aromatic group which may have a substituent (with the proviso that $R^1$ and $R^2$ are different groups), and $R^4$ represents an aliphatic group which may have a substituent, or an aromatic group which may have a substituent (with the proviso that when the $R^1$ is the aromatic group which may have a substituent, the $R^4$ is the aliphatic group which may have a substituent).

<3> A compound represented by the following General Formula (1):

General Formula (1)

where in the General Formula (1), $R^1$ and $R^2$ each represent an aliphatic group which may have a substituent, or an aromatic group which may have a substituent (with the proviso that $R^1$ and $R^2$ are different groups), $R^3$ represents an aromatic group which may have a substituent, and $R^4$ represents an aliphatic group which may have a substituent, or an aromatic group which may have a substituent.

<4> A method for producing the compound represented by General Formula (1) according to <3>, the method including:

reacting a compound represented by the following General Formula (3) and a compound represented by the following General Formula (4):

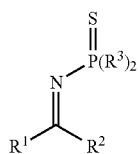

General Formula (3)

where in the General Formula (3), $R^1$ and $R^2$ each represent an aliphatic group which may have a substituent, or an aromatic group which may have a substituent (with the proviso that $R^1$ and $R^2$ are different groups), and $R^3$ represents an aromatic group which may have a substituent,

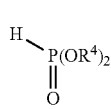

General Formula (4)

where in the General Formula (4), $R^4$ represents an aliphatic group which may have a substituent, or an aromatic group which may have a substituent.

<5> The method according to <4>, wherein the reacting is performed using a catalyst containing an asymmetric ligand.

<6> The method according to <5>, wherein the catalyst containing an asymmetric ligand is a copper-optically active phosphine complex.

INDUSTRIAL APPLICABILITY

The novel method of the present invention for producing the compound is capable of synthesizing various optically active α-aminophosphonic acid derivatives without using chiral compounds in a large amount, and therefore can be suitably used for production of optically active α-aminophosphonic acid derivatives.

The novel compound represented by the General Formula (1) of the present invention can be suitably used for the synthesis of optically active α-aminophosphonic acid derivatives.

The invention claimed is:

1. A method for producing an optically active α-aminophosphonic acid derivative, the method comprising:
converting a compound represented by the following General Formula (1) to an optically active α-aminophosphonic acid derivative represented by the following General Formula (2):

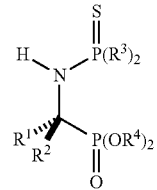

General Formula (1)

where in the General Formula (1), $R^1$ and $R^2$ each represent an aliphatic group which may have a substituent, or an aromatic group which may have a substituent (with the proviso that $R^1$ and $R^2$ are different groups), $R^3$ represents an aromatic group which may have a substituent, and $R^4$ represents an aliphatic group which may have a substituent, or an aromatic group which may have a substituent,

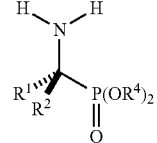

General Formula (2)

where in the General Formula (2), $R^1$ and $R^2$ each represent an aliphatic group which may have a substituent, or an aromatic group which may have a substituent (with the proviso that $R^1$ and $R^2$ are different groups), and $R^4$ represents an aliphatic group which may have a substituent, or an aromatic group which may have a substituent.

2. An optically active α-aminophosphonic acid derivative represented by the following General Formula (2):

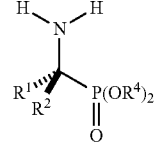

General Formula (2)

where in the General Formula (2), $R^1$ represents an aliphatic group having a substituent, an unsaturated aliphatic group, a cyclic alkyl group, an n-propyl group, an isopropyl group, an isobutyl group, a sec-butyl group, an n-pentyl group, an isopentyl group, a neopentyl group, a tert-pentyl group, a 1-methylbutyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, an isooctyl group, a nonyl group, a decyl group, an undecyl group, a dodecyl group, a tridecyl group, a tetradecyl group, a pentadecyl group, a hexadecyl group, a heptadecyl group, an octyldecyl group, a nonadecyl group, an icosyl group, an aromatic group having a substituent, a 1-naphthyl group, or a 2 naphthyl group, $R^2$ represents an aliphatic group which may have a substituent, or an aromatic group which may have a substituent (with the proviso that $R^1$ and $R^2$ are different groups), and $R^4$ represents an aliphatic group which may have a substituent, or an aromatic group which may have a substituent (with the proviso that when the $R^1$ is the aromatic group which may have a substituent, the $R^4$ is the aliphatic group which may have a substituent).

3. A compound represented by the following General Formula (1):

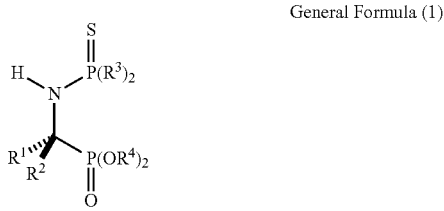

General Formula (1)

where in the General Formula (1), $R^1$ and $R^2$ each represent an aliphatic group which may have a substituent, or an aromatic group which may have a substituent (with the proviso that $R^1$ and $R^2$ are different groups), $R^3$ represents an aromatic group which may have a substituent, and $R^4$ represents an aliphatic group which may have a substituent, or an aromatic group which may have a substituent.

4. A method for producing a compound represented by the following General Formula (1), the method comprising:
reacting a compound represented by the following General Formula (3) and a compound represented by the following General Formula (4):

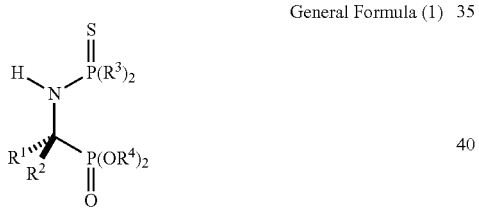

General Formula (1)

where in the General Formula (1), $R^1$ and $R^2$ each represent an aliphatic group which may have a substituent, or an aromatic group which may have a substituent (with the proviso that $R^1$ and $R^2$ are different groups), $R^3$ represents an aromatic group which may have a substituent, and $R^4$ represents an aliphatic group which may have a substituent, or an aromatic group which may have a substituent,

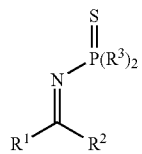

General Formula (3)

where in the General Formula (3), $R^1$ and $R^2$ each represent an aliphatic group which may have a substituent, or an aromatic group which may have a substituent (with the proviso that $R^1$ and $R^2$ are different groups), and $R^3$ represents an aromatic group which may have a substituent,

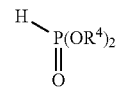

General Formula (4)

where in the General Formula (4), $R^4$ represents an aliphatic group which may have a substituent, or an aromatic group which may have a substituent.

5. The method according to claim 4, wherein the reacting is performed using a catalyst containing an asymmetric ligand.

6. The method according to claim 5, wherein the catalyst containing an asymmetric ligand is a copper-optically active phosphine complex.

* * * * *